United States Patent
Skuratovich et al.

(10) Patent No.: US 9,642,884 B1
(45) Date of Patent: May 9, 2017

(54) CANNABINOID ALCOHOLIC DRINKS (CADS) AND METHOD FOR PRODUCING CADS

(71) Applicants: Olga Skuratovich, Denver, CO (US); Filipp Mirzakhanov, Centennial, CO (US)

(72) Inventors: Olga Skuratovich, Denver, CO (US); Filipp Mirzakhanov, Centennial, CO (US)

( * ) Notice: Subject to any disclaimer, the term of this patent is extended or adjusted under 35 U.S.C. 154(b) by 0 days.

(21) Appl. No.: 15/044,110

(22) Filed: Feb. 16, 2016

(51) Int. Cl.
*A01N 65/00* (2009.01)
*A61K 36/185* (2006.01)
*C12G 3/04* (2006.01)
*A61K 9/00* (2006.01)

(52) U.S. Cl.
CPC .......... *A61K 36/185* (2013.01); *A61K 9/0095* (2013.01); *C12G 3/04* (2013.01)

(58) Field of Classification Search
CPC ...................................................... A61K 36/00
USPC ......................................................... 424/725
See application file for complete search history.

(56) References Cited

U.S. PATENT DOCUMENTS

2016/0158299 A1* 6/2016 Bohus ................. A61K 36/185
424/725

OTHER PUBLICATIONS

Interactions among the cannabinoids (thc, cbd and cbn) alone and when combined with ethanol. Effects on human performance, Bird KD, Boleyn T, Chesher GB, Jackson DM, Starmer GA, Teo RKC. Proc. Int. Counc. Alcohol Drugs Traffic Safety Conf. 1981; 1981: 1111-1125. [abstract only].

Transdermal Delivery of Cannabidiol Attenuates Binge Alcohol-induced Neurodegeneration in a Rodent Model of an Alcohol Use Disorder , Liput D, hamell D, Stinchcomb A., Nixon K. Pharmacology Biochemistry and Behavior vol. 111, Oct. 2013, pp. 120-127 [abstract only].

Comparison of Cannabidiol, Antioxidants, and Diuretics in Reversing Binge Ethanol-Induced Neurotoxicity, Hamelink, C, Hampson A, Wink D, Eiden L, Eskay R., The Journal of Pharmacology and Experimental Therapeutics 314:780-788, 2005.

* cited by examiner

*Primary Examiner* — Michael Meller
(74) *Attorney, Agent, or Firm* — Hoban Law Group; Kevin H. Fortin

(57) ABSTRACT

Cannabinoid Alcoholic Drinks (CADs) and methods for producing CADs utilize cannabinoids dissolved in ethanol. The resulting cannabinoid/ethanol solution is then combined with one or more consumable alcohols to create a CAD. Cannabidiol (CBD) can be selected as the cannabinoid, and the solution of CBD and ethanol is called CBD/ethanol solution and combining it with one or more consumable alcohols yields a CAD.

1 Claim, 2 Drawing Sheets

CANNABINOID ALCOHOLIC DRINKS (CADS) AND METHOD FOR PRODUCING CADS

TECHNICAL FIELD

The present invention relates generally to the fields of plant extracts and their isolates and alcohols designed for consumption, more particularly to a combination of one or more cannabinoids (such as cannabidiol, also known as "CBD") and ethanol, that can then be combined with alcoholic drinks to form Cannabinoid Alcoholic Drinks (CADs), and including one or more methods for producing CADs.

BACKGROUND

Humans have been utilizing plant extracts for thousands of years. Early medicines were sourced almost exclusively from plants and new drugs/medications are developed from plants to this day. Additionally, humans have produced ethanol for consumption for thousands of years as well. However, as pure ethanol is generally unpalatable, most alcoholic drinks contain only a percentage of ethanol, with the remaining percentage comprising water, colorings, flavorings, and other components, depending on the particular alcohol in question.

The deleterious effects of consuming alcohol are well known, especially when consumed to excess and/or chronically. In such cases, alcohol consumption can: negatively impact the nervous system (including, especially, the brain); increase the risk of hemorrhagic stroke; lead to widespread and significant brain lesions; cause impaired prospective memory and impaired cognitive ability; increase the risk of serious cognitive decline and a range of neuropsychiatric complications; cause dampened activation in brain networks responsible for emotional processing; result in alcohol-related brain damage; cause alcohol-related dementia; lead to increased risk of major depressive disorders; increase incidences of other mental health disorders; and significantly increase the risk of suicide.

Despite these known health risks, alcohol continues to be consumed all across the world. What is needed is a way to mitigate or potentially offset some of these negative consequences to the brain and nervous system due to alcohol consumption.

As noted above, many plant extracts and their isolated constituents have medicinal qualities. One in particular, cannabidiol ("CBD") which is from a group called cannabinoids, has been shown to have significant neuroprotective effects. Various studies have determined that cannabidiol can attenuate binge alcohol-induced neurodegeneration (see, for example, "Transdermal Delivery of Cannabidiol Attenuates Binge Alcohol-induced Neurodegeneration in a Rodent Model of an Alcohol Use Disorder," Daniel J. Liputa, et al., Pharmacology Biochemistry and Behavior, vol. 111, October 2013, Pgs. 120-127). Thus, co-administration of CBD with alcohol can help to mitigate the damage and dangers associated with alcohol consumption. However, co-administration of alcoholic drinks and CBD by alternative routes of administration (such as transdermal, sublingual etc) is unlikely to be employed due to subject convenience and compliance.

Therefore, what is needed is a composition of matter that provides for the stable infusion of CBD into consumable alcohol, so that it can be easily co-administered. Also, a method for producing CADs is needed.

DETAILED DESCRIPTION

Figure 1:
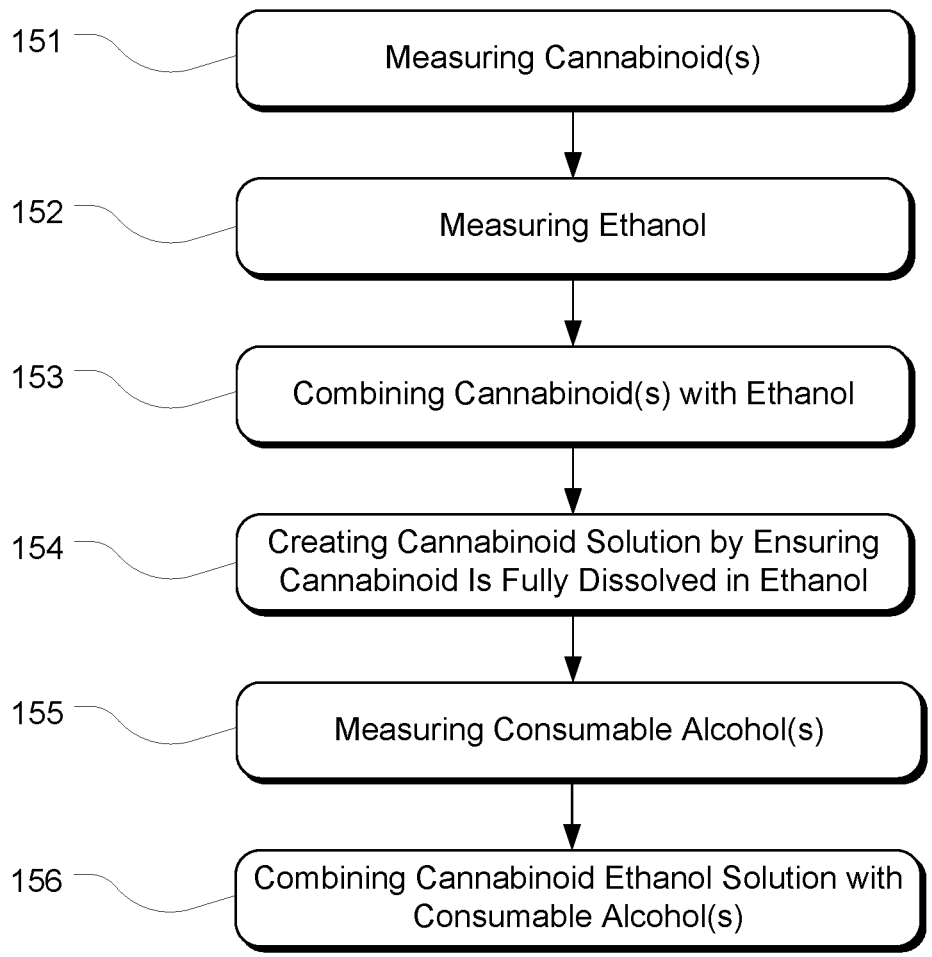
FIG. 1 illustrates a perspective view of an exemplary embodiment of steps for a method for producing CADs.

In the following discussion, numerous specific details are set forth to provide a thorough understanding of the present disclosure. However, those skilled in the art will appreciate that embodiments may be practiced without such specific details. Furthermore, lists and/or examples are often provided and should be interpreted as exemplary only and in no way limiting embodiments to only those examples.

Exemplary embodiments are described below in the accompanying Figure. The following detailed description provides a comprehensive review of the drawing in order to provide a thorough understanding of, and an enabling description for, these embodiments. One having ordinary skill in the art will understand that in some cases well-known structures and functions have not been shown or described in detail to avoid unnecessarily obscuring the description of the embodiments.

Referring now to the drawing, FIG. 1 illustrates a perspective view of an exemplary embodiment of steps for a method for producing CADs 150. In this particular embodiment, any cannabinoids (or a combination thereof) can be utilized. For another embodiment utilizing a specific cannabinoid, in this case CBD, see FIG. 2.

In the exemplary embodiment of FIG. 1, the Measuring Cannabinoid(s) step 151 involves measuring the amount of isolated cannabinoid. In one embodiment, 7.8 milligrams of isolated cannabinoid is measured in a beaker. Other embodiments can utilize other amounts in other types of containers.

In the Measuring Ethanol step 152, five milliliters of ethanol is measured in a graduated cylinder in the embodiment illustrated in FIG. 1. In other embodiments, other amounts can be measured in other containers.

In the Combining Cannabinoid(s) with Ethanol step 153, the cylinder of ethanol from 152 can be poured into the beaker of cannabinoid from 151. In another embodiment, the cannabinoid from 151 is added to the ethanol from 152.

In the embodiment shown in FIG. 1, the step of Creating Cannabinoid Solution by Ensuring Cannabinoid Is Fully Dissolved in Ethanol 154 involves stirring, agitating, or otherwise ensuring that the cannabinoid from 151 is fully dissolved in the ethanol from 152 in order to create a cannabinoid solution. If there is too much cannabinoid to fully dissolve in the amount of ethanol used, either increase the ethanol amount or decrease the amount of cannabinoid until the solution is created and the cannabinoid does not precipitate back out.

The Measuring Consumable Alcohol(s) step 155 involves measuring a plurality of alcohols (i.e., one or more) in preparation for addition of the solution from 154.

The Combining Cannabinoid Solution with Consumable Alcohol(s) step 156 involves adding the Solution from 154 to a plurality of consumable alcohols measured in 155 in order to create a CAD. In one example, 50 mg of isolated cannabinoid is measured 151. Approximately 5 mL of ethanol is measured 152. The cannabinoid is combined with the ethanol 153. A cannabinoid solution is created by ensuring the cannabinoid is fully dissolved in the ethanol 154. The resulting solution is then combined with one or more consumable alcohols 156—in this example, approximately 745 mL of vodka, to create a standard 750 mL bottle of cannabinoid infused vodka. In other embodiments, other volumes of CADs can be produced. In yet another embodiment, the volume fraction of cannabinoid/ethanol solution in total volume of CADs is equal to or less than 1%.

In the example described above, the alcohol utilized is vodka. In other embodiments, one or more other alcohols can be utilized. Additionally, it is contemplated that other substances besides alcohols could also be utilized (for example, fruit juice).

One particular cannabinoid that can be used is CBD. Testing has shown that CBD will not precipitate out given the amounts/ratios described above. Thus, the CBD and ethanol combine to remain as a fully dissolved, clear solution. It should be noted that no heating or cooling of the components or solution is needed, as the methods can be practiced at room temperature (although other temperatures may have beneficial effects).

Figure 2:
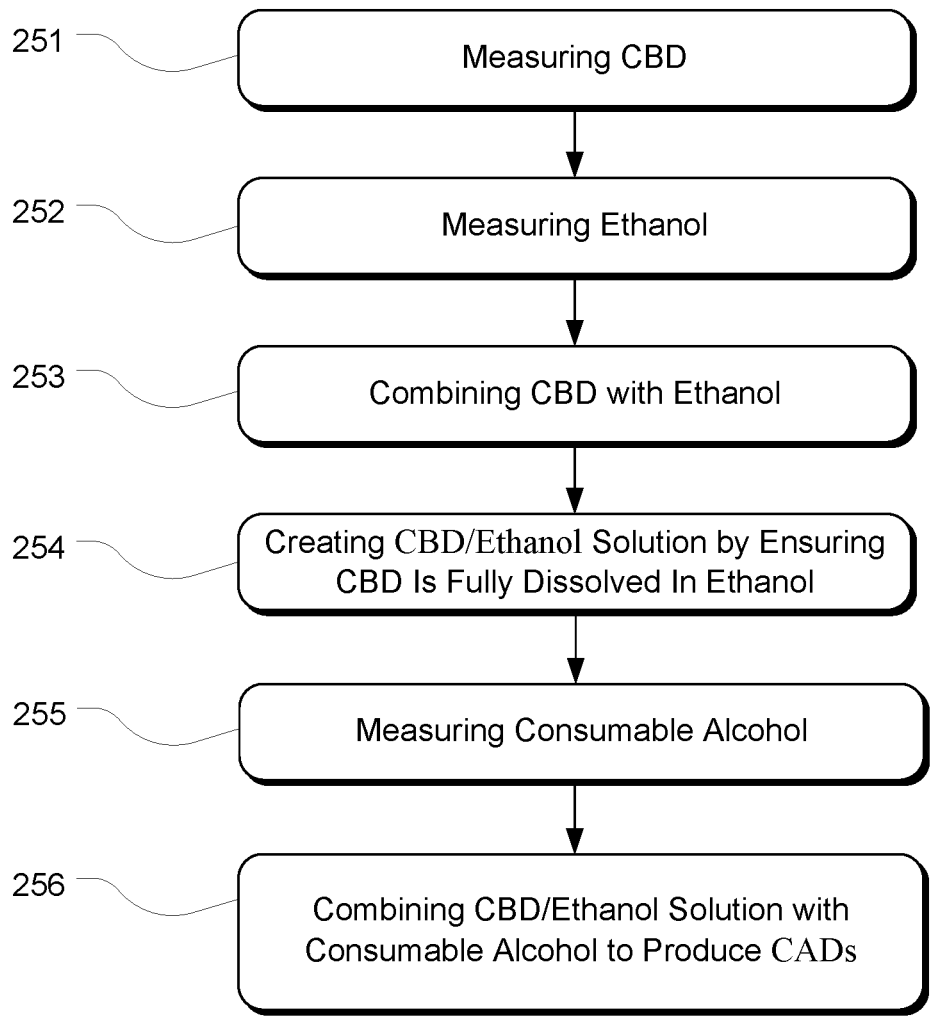
FIG. 2 illustrates a perspective view of an exemplary embodiment of steps for a method for producing CADs with CBD.

FIG. 2 illustrates a perspective view of an exemplary embodiment of steps for a method for producing CADs 250. In this particular embodiment, a particular cannabinoid, CBD, is utilized.

In the exemplary embodiment of FIG. 2, the Measuring CBD step 251 involves measuring the amount of CBD. In one embodiment, 7.8 milligrams of isolated cannabinoid is measured in a beaker. Other embodiments can utilize other amounts in other types of containers.

In the Measuring Ethanol step 252, ten milliliters of ethanol is measured in a graduated cylinder in the embodiment illustrated in FIG. 2. In other embodiments, other amounts can be measured and other containers can be used.

In the Combining CBD with Ethanol step 253, the cylinder of ethanol from 252 can be poured into the beaker of CBD from 251. In another embodiment, the CBD from 251 is added to the ethanol from 252.

In the embodiment shown in FIG. 2, the step of Creating CBD/ethanol Solution by Ensuring CBD Is Fully Dissolved in Ethanol 254 involves stirring, agitating, or otherwise ensuring that the CBD from 251 is fully dissolved in the ethanol from 252 in order to create a CBD/ethanol solution. If there is too much CBD to fully dissolve in the amount of ethanol used, one can increase the ethanol amount or decrease the amount of CBD until the solution is created and the CBD does not precipitate back out.

The Measuring Consumable Alcohol(s) step 255 involves measuring a plurality of consumable alcohols (i.e., one or more) in preparation for addition of the solution from 254.

The Combining CBD/Ethanol Solution with consumable Alcohol(s) step 256 involves adding the Solution from 254 to the plurality of consumable alcohols measured in 255 in order to create a CAD. In one example, 50 mg of isolated CBD is measured 251. Approximately 5 mL of ethanol is measured 252. The CBD is combined with the ethanol 253. A CBD/Ethanol solution is created by ensuring the CBD is fully dissolved in the ethanol 254. The resulting solution is then combined 256 with one or more consumable alcohols 255, in this example, approximately 745 mL of vodka to create a standard 750 mL bottle of CBD infused vodka.

In the example described above, the alcohol utilized is vodka. In other embodiments, one or more other alcohols can be utilized. Additionally, it is contemplated that other substances besides consumable alcohols could also be utilized (for example, fruit juice) in yet other embodiments.

In another embodiment, 10 mg of CBD and 5 mL of ethanol were utilized. The resulting CBD/Ethanol solution was then added to a beaker of 145 mL of vodka, again yielding a concentration of 0.067 mg/mL. The result is a clear CBD/Ethanol alcohol.

When consumed, the positive effects of the CBD help to offset the deleterious effects of the alcohol. Instead of impaired cognitive function, many report euphoria, a sense of being upbeat and feeling little to no effect of the alcohol.

As described above, vodka can be generally used as the consumable alcohol in question. However, other consumable alcohol(s) can be employed without departing from the scope of the invention as the process does not necessarily change (except for potentially varying the amounts utilized). Since the cannabinoid ethanol solution is relatively small in proportion to the alcohol, little if any change is made to the flavor, color, consistency, etc. of the consumable alcohol by its addition.

In yet another embodiment, 1 mL of ethanol was utilized with 7.8 mg of CBD. There was no problem with dissolution and it is concluded that very small amounts of ethanol can be used to dissolve CBD. Consequently, drink quality would not suffer much from the addition of such small amounts of pure ethanol to whichever consumable alcohol is used (in this example, tequila).

While particular embodiments have been described and disclosed in the present application, it is clear that any number of permutations, modifications, or embodiments may be made without departing from the spirit and the scope of this disclosure.

Particular terminology used when describing certain features or aspects of the embodiments should not be taken to imply that the terminology is being redefined herein to be restricted to any specific characteristics, features, or aspects with which that terminology is associated. In general, the terms used in the following claims should not be construed to be limited to the specific embodiments disclosed in the specification, unless the above Detailed Description section explicitly defines such terms. Accordingly, the actual scope of the claims encompasses not only the disclosed embodiments, but also all equivalent ways of practicing or implementing the claimed subject matter.

The above detailed description of the embodiments is not intended to be exhaustive or to limit the invention to the precise embodiment or form disclosed herein or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

Any patents, applications and other references that may be listed in accompanying or subsequent filing papers, are incorporated herein by reference. Aspects of the invention can be modified, if necessary, to employ the systems, functions, and concepts of the various references to provide yet further embodiments of the invention.

In light of the above "Detailed Description," the Inventor may make changes to the invention. While the detailed description outlines possible embodiments of the invention and discloses the best mode contemplated, no matter how detailed the above appears in text, the invention may be practiced in a myriad of ways. Thus, implementation details may vary considerably while still being encompassed by the spirit of the invention as disclosed by the inventors. As discussed herein, specific terminology used when describing certain features or aspects of the invention should not be taken to imply that the terminology is being redefined herein to be restricted to any specific characteristics, features, or aspects of the invention with which that terminology is associated.

While certain aspects of the invention are presented below in certain claim forms, the inventors contemplate the various aspects of the invention in any number of claim forms. Accordingly, the inventors reserve the right to add additional claims after filing the application to pursue such additional claim forms for other aspects of the invention.

The above specification, examples and data provide a description of the structure and use of exemplary implementations of the described articles of manufacture and methods. It is important to note that many implementations can be made without departing from the spirit and scope of the invention.

What is claimed is:

1. A method for producing a cannabidiol/vodka drink the method comprising:
   a) providing 7.8 mg of isolated cannabidiol;
   b) providing 1 ml to 10 ml of vodka; and
   c) combining the vodka and the cannabidiol to create the cannabidiol/vodka drink, wherein the cannabidiol is fully dissolved in the vodka.

* * * * *